(12) United States Patent
Schmitt et al.

(10) Patent No.: US 8,663,302 B2
(45) Date of Patent: Mar. 4, 2014

(54) DELIVERY SYSTEM EJECTION COMPONENT AND METHOD

(75) Inventors: Joshua J. Schmitt, Santa Rosa, CA (US); Jeffery Argentine, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 980 days.

(21) Appl. No.: 12/759,420

(22) Filed: Apr. 13, 2010

(65) Prior Publication Data

US 2011/0251666 A1 Oct. 13, 2011

(51) Int. Cl.
*A61F 2/06* (2013.01)

(52) U.S. Cl.
USPC .......................................... 623/1.11

(58) Field of Classification Search
USPC ............... 606/108; 623/1.11, 1.12, 1.13, 1.23
See application file for complete search history.

(56) References Cited

U.S. PATENT DOCUMENTS

| | | | |
|---|---|---|---|
| 5,891,193 A | 4/1999 | Robinson et al. | |
| 6,607,529 B1 * | 8/2003 | Jones et al. | 606/47 |
| 7,264,632 B2 * | 9/2007 | Wright et al. | 623/1.12 |
| 2008/0021538 A1 | 1/2008 | Wright et al. | |
| 2008/0114442 A1 | 5/2008 | Mitchell et al. | |
| 2008/0114443 A1 | 5/2008 | Mitchell et al. | |

FOREIGN PATENT DOCUMENTS

| | | |
|---|---|---|
| EP | 0657147 | 6/1995 |
| EP | 1369098 | 12/2003 |
| EP | 1440673 | 7/2004 |
| WO | WO2008/112399 | 9/2008 |

OTHER PUBLICATIONS

U.S. Appl. No. 12/426,020, filed Apr. 17, 2009, Glynn et al.

* cited by examiner

*Primary Examiner* — Victor Nguyen

(57) ABSTRACT

A stent or stent-graft delivery system includes a stent ejection component. The stent ejection component includes a body and an ejection collar. The ejection collar extends from the body in the proximal direction. The ejection collar assists in automatically ejecting a proximal end of a stent when the tapered tip is moved in the distal direction to deploy the stent. A stent or stent-graft delivery system may also include a retain-sleeve landing component. The retaining-sleeve landing component includes a body and a landing collar. The landing collar extends from the body in a distal direction. The landing collar automatically captures a tapered tip of the delivery system when the tapered tip is moved in a distal direction to deploy a stent contained in the delivery system. Upon capture of the tapered tip, the stent ejection component with the tapered tip attached has an atraumatic profile.

17 Claims, 8 Drawing Sheets

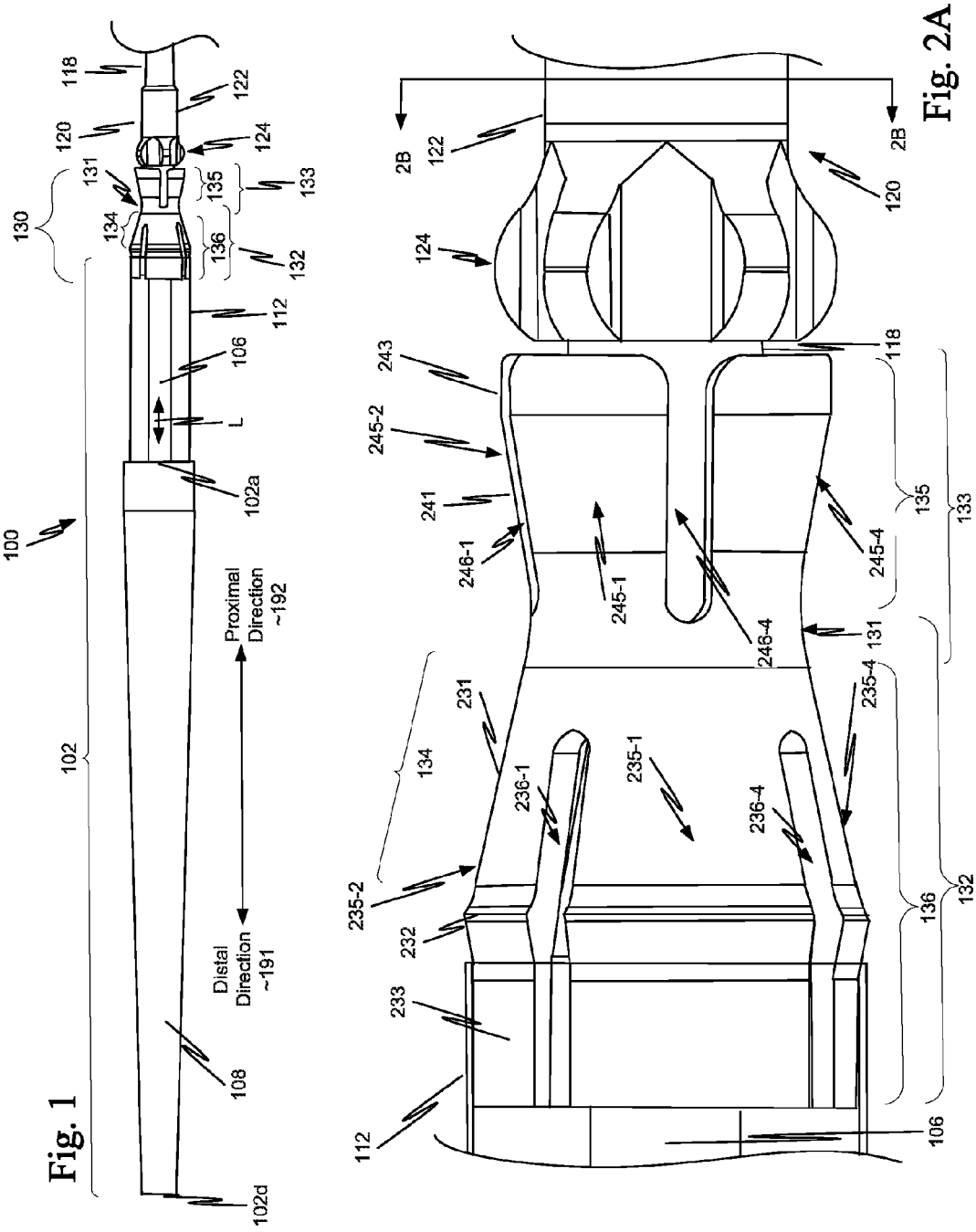

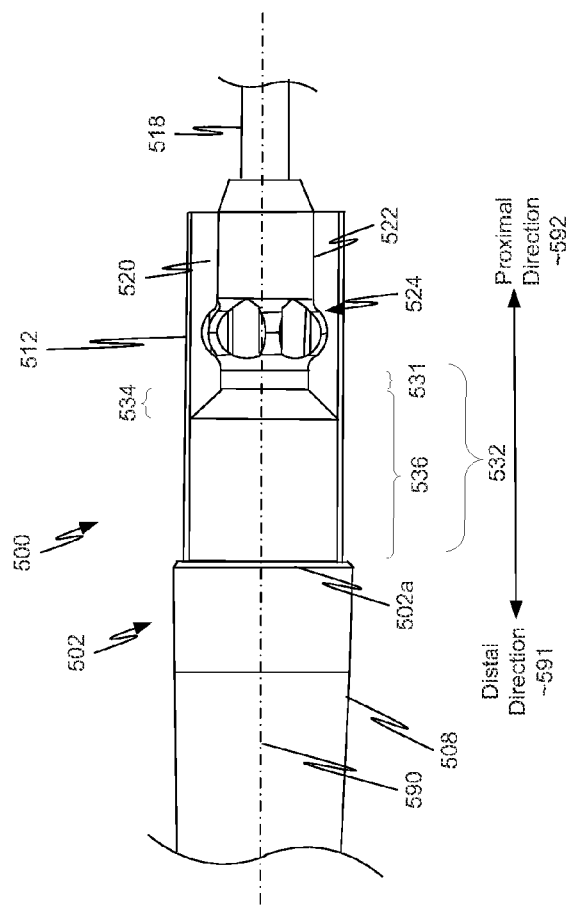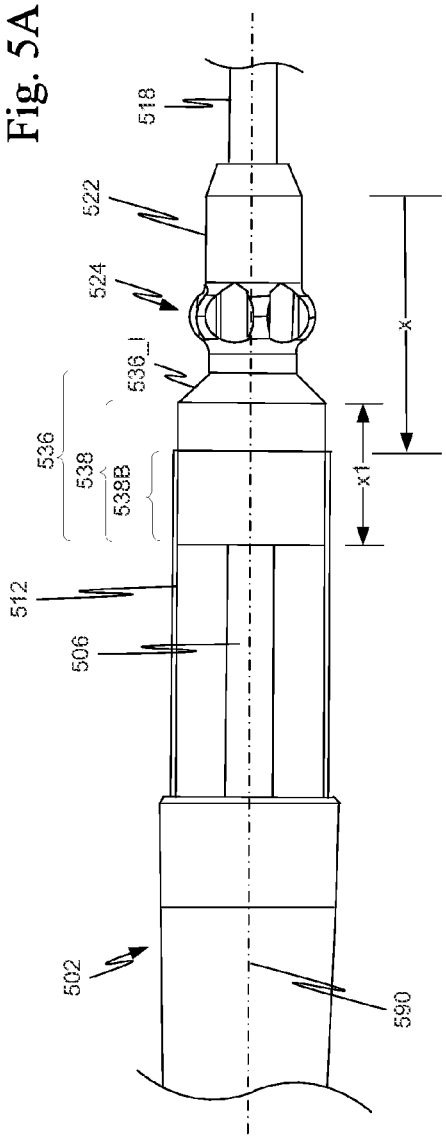

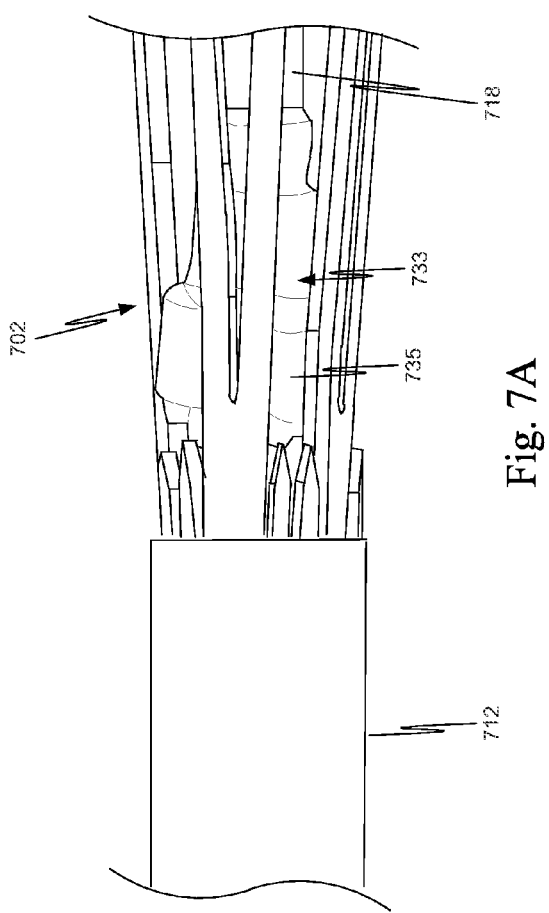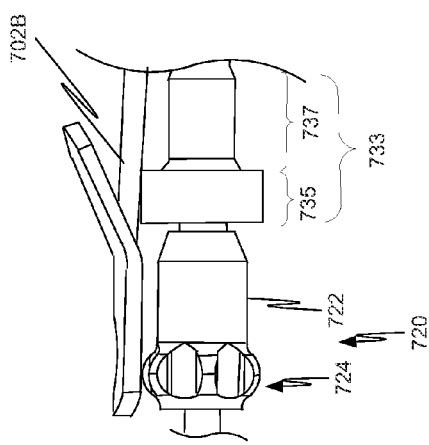
Fig. 7A
Fig. 7B

DELIVERY SYSTEM EJECTION COMPONENT AND METHOD

BACKGROUND

1. Field of Invention

This invention relates generally to medical devices and procedures, and more particularly to a method and system of deploying a stent in a vascular system.

2. Related Art

Prostheses for implantation in blood vessels or other similar organs of the living body are, in general, well known in the medical art. For example, prosthetic vascular grafts formed of biocompatible materials (e.g., Dacron or expanded polytetrafluoroethylene (ePTFE) tubing) have been employed to replace or bypass damaged or occluded natural blood vessels.

A graft tube material supported by a framework is known as a stent-graft or endoluminal graft. In general, the use of stents and stent-grafts for treatment or isolation of vascular aneurysms and vessel walls which have been thinned or thickened by disease (endoluminal repair or exclusion) is well known.

Many stents and stent-grafts are "self-expanding", i.e., inserted into the vascular system in a compressed or contracted state, and permitted to expand upon removal of a restraint. Self-expanding stents and stent-grafts typically employ a wire or tube configured (e.g., bent or cut) to provide an outward radial force and employ a suitable elastic material such as stainless steel or nitinol (nickel-titanium). Nitinol may additionally employ shape memory properties.

The self-expanding stent or self-expanding stent-graft is typically configured in a tubular shape, sized to have a slightly greater diameter than the diameter of the blood vessel in which the stent or stent-graft is intended to be used. In general, rather than inserting it in a traumatic and invasive manner using open surgery, stents and stent-grafts are typically deployed through a less invasive intraluminal delivery, i.e., cutting through the skin to access a lumen or vasculature or percutaneously via successive dilatation, at a convenient (and less traumatic) entry point, and routing the compressed stent or stent-graft in a delivery system through the lumen to the site where the prosthesis is to be deployed.

Intraluminal deployment in one example is effected using a delivery catheter with coaxial inner tube, sometimes called an inner tube (plunger), and an outer tube, sometimes called the sheath, arranged for relative axial movement. The stent or stent-graft is compressed and disposed within the distal end of the sheath in front of the inner tube.

The catheter is then maneuvered, typically routed though a vessel (e.g., lumen), until the end of the catheter containing the stent or stent-graft is positioned in the vicinity of the intended treatment site. The inner tube is then held stationary while the sheath of the delivery catheter is withdrawn. The inner tube prevents the stent-graft from moving back as the sheath is withdrawn.

As the sheath is withdrawn, the stent or stent-graft is gradually exposed from its proximal end to its distal end. The exposed portion of the stent or stent-graft radially expands so that at least a portion of the expanded portion is in substantially conforming surface contact with a portion of the interior of the blood vessel wall.

The proximal end of the stent or stent-graft is the end closest to the heart by way of blood flow path whereas the distal end of the stent or stent-graft is the end furthest away from the heart during deployment. In contrast and of note, the distal end of the catheter is usually identified to the end that is farthest from the operator (handle) while the proximal end of the catheter is the end nearest the operator (handle).

For purposes of clarity of discussion, as used herein, the distal end of the catheter is the end that is farthest from the operator (the end furthest from the handle) while the distal end of the stent-graft is the end nearest the operator (the end nearest the handle or the handle itself), i.e., the distal end of the catheter and the proximal end of the stent-graft are the ends furthest from the handle while the proximal end of the catheter and the distal end of the stent-graft are the ends nearest the handle. However, those of skill in the art will understand that depending upon the access location, the distal and proximal end descriptors for the stent-graft and delivery system description may be consistent or opposite in actual usage.

Some self-expanding stent deployment systems and stent-graft deployment systems are configured to have each exposed increment of the stent or stent graft at the proximal end of the stent-graft deploy (flare out or mushroom) as the sheath is pulled back. The proximal end of the stent-graft is typically designed to expand to fixate and seal the stent-graft to the wall of the vessel during deployment. Such a configuration leaves little room for error in placement since re-positioning the stent-graft after initial deployment, except for a minimal pull down retraction, is difficult, if possible at all. The need to achieve accurate proximal end positioning of the stent-graft first makes accurate pre-deployment positioning of the stent or stent-graft critical.

SUMMARY

In one example, a stent or stent-graft delivery system includes a retaining-sleeve landing component. The retaining-sleeve landing component includes a body and a landing collar, which are fixedly mounted on a spindle tube. In another example, a stent or stent-graft delivery system includes a stent ejection component. The stent ejection component includes a body and an ejection collar, which are fixedly mounted on a spindle tube. In still yet another example, a stent or stent-graft delivery system includes both the retaining-sleeve landing component and the stent ejection component.

In the examples with a retaining-sleeve landing component, the landing collar extends from the body of the retaining-sleeve landing component in a distal direction. The landing collar automatically distally and centrally captures a tapered tip of the delivery system when the tapered tip is moved in a distal direction to deploy a stent contained in the delivery system. Herein, automatic capture means that the tapered tip is captured on the landing collar as a result of the distal motion of the tapered tip to deploy the stent and no other action is required on the part of the operator to facilitate the capture. Upon capture of the tapered tip, the landing collar with the tapered tip attached has an atraumatic profile in a proximal direction.

The automatic capture of the tapered tip eliminates the need to capture the tip after deployment of the stent by the delivery system. Such tip capture was previously required for some conventional stent delivery systems. The elimination of the tip capture sequence decreases the time required for the procedure being performed using the stent delivery system. A shorter procedure time has numerous benefits as is known to those knowledgeable in the field.

In addition, when the retaining-sleeve landing component with the tapered tip attached is withdrawn from the patient, the atraumatic profile inhibits the tapered tip from snagging on the deployed stent. Thus, the atraumatic profile eliminates the problem of snagging the stent, which was encountered when withdrawing a tapered tip in some conventional stent delivery systems.

In the examples with a stent ejection component, the ejection collar assists in automatically ejecting a proximal end of a stent when the tapered tip is moved in the distal direction to deploy the stent. Specifically, the ejection collar assures that the apexes, sometimes referred to as crowns, of the stent are released from a spindle of the delivery system. The ejection collar assists the natural self-expanding force of the stent. The additional force supplied by the ejection collar is sufficient to eject any crowns of the stent that may be stuck on the spindle. Thus, the ejection collar helps in deploying the stent at the desired location with a particular orientation. Any potential issues with the stent binding on the spindle are ameliorated with the ejection collar.

The graft delivery system includes a spindle tube with a spindle attached to the spindle tube. The retaining-sleeve landing component also is fixed to the spindle tube. Here, fixed to the spindle tube means that when the spindle tube moves the retaining-sleeve landing component moves with the spindle tube. The retaining-sleeve landing component includes a body and a landing collar extending distally from the body.

In one example, the landing collar further includes a plurality of cantilevered landing beams. Adjacent cantilevered landing beams are separated by a slot. In this example, each cantilevered landing beam, in the plurality of cantilevered landing beams, includes an atraumatic profile.

At least one cantilevered landing beam in the plurality of cantilevered landing beams includes a ridge; and an inclined portion extending from the body to the ridge. The at least one cantilevered beam also includes a landing tab extending distally from the ridge. An outer radius of the ridge is greater than an outer radius of the landing tab.

The graft delivery system also includes a tube, extending through the spindle tube. The tube has a distal end. A tip, mounted on the distal end of the tube, includes a retaining sleeve. The retaining sleeve is a proximal portion of the tip, and the retaining sleeve is movable over the retaining-sleeve landing component.

The landing collar includes an element with an outer radius greater than an inner radius of the retaining sleeve. In one example, this element is a ridge. An outer radius of the ridge is greater than an outer radius of the body so that the landing collar includes the atraumatic profile between the body and the ridge.

In another example, the landing collar includes a hollow cylinder having an outer circumferential surface of substantially uniform radius. The hollow cylinder is a distal portion of the landing collar. A proximal portion of this landing collar has an atraumatic profile. The distal portion of the landing collar has a length so that at least part of the distal portion remains within the retaining sleeve following stent deployment.

The stent graft delivery system is used in a method that moves a tip of the stent graft delivery system in a distal direction. The tip is mounted on an inner tube of the delivery system and the tip includes a retaining sleeve at a proximal end of the tip. The method captures the retaining sleeve on a landing collar attached to an outer tube of the graft delivery system as a result of the moving. The inner tube moves through the outer tube.

Returning to the stent ejection component, in one example, the ejection collar extends proximally from the body of the stent ejection component. The body of the stent ejection component is distal to the spindle pins of a spindle mounted on the spindle tube. The ejection collar includes a plurality of cantilevered ejection beams. Adjacent cantilevered ejection beams are separated by a slot.

At least one cantilevered landing beam in the plurality of cantilevered landing beams includes an ejection tab, and an inclined portion extending from the body to the ejection tab. When a stent is constrained on spindle pins of the spindle by the retaining sleeve, the at least ejection beam is compressed radially inward (compressed) so that the ejection tab is positioned under a crown of the stent.

In another example of the stent ejection component, the ejection collar extends distally from the body of the stent ejection component. The body of the stent ejection component is proximal to a spindle mounted on the spindle tube.

In this example, the ejection collar is a hollow cylinder having a longitudinal axis coincident with the longitudinal axis of the spindle tube. The ejection collar components (elements) comprise a material having elastic deformation properties. When a stent is constrained on spindle pins of the spindle by the retaining sleeve, the ejection collar is elastically deformed by the stent. When the stent is no longer constrained by the retaining sleeve, the energy of the constrained ejection collar is released to cause the collar elements to spring radially outward to help move crowns of the stent off the spindle pins.

BRIEF DESCRIPTION OF THE DRAWINGS

FIG. 1 is an illustration of a distal end of a delivery system that includes a component having both a stent ejection component and a retaining-sleeve landing component.

FIG. 2A is a close-up view of the component and spindle of FIG. 1.

FIGS. 5A and 5B illustrate another example of a retaining-sleeve landing component, which includes a body and a landing collar.

FIGS. 7A and 7B schematically illustrate progressive steps in the deployment of a stent by the delivery system that includes the stent ejection component of FIGS. 6A and 6B.

Figure 2B:
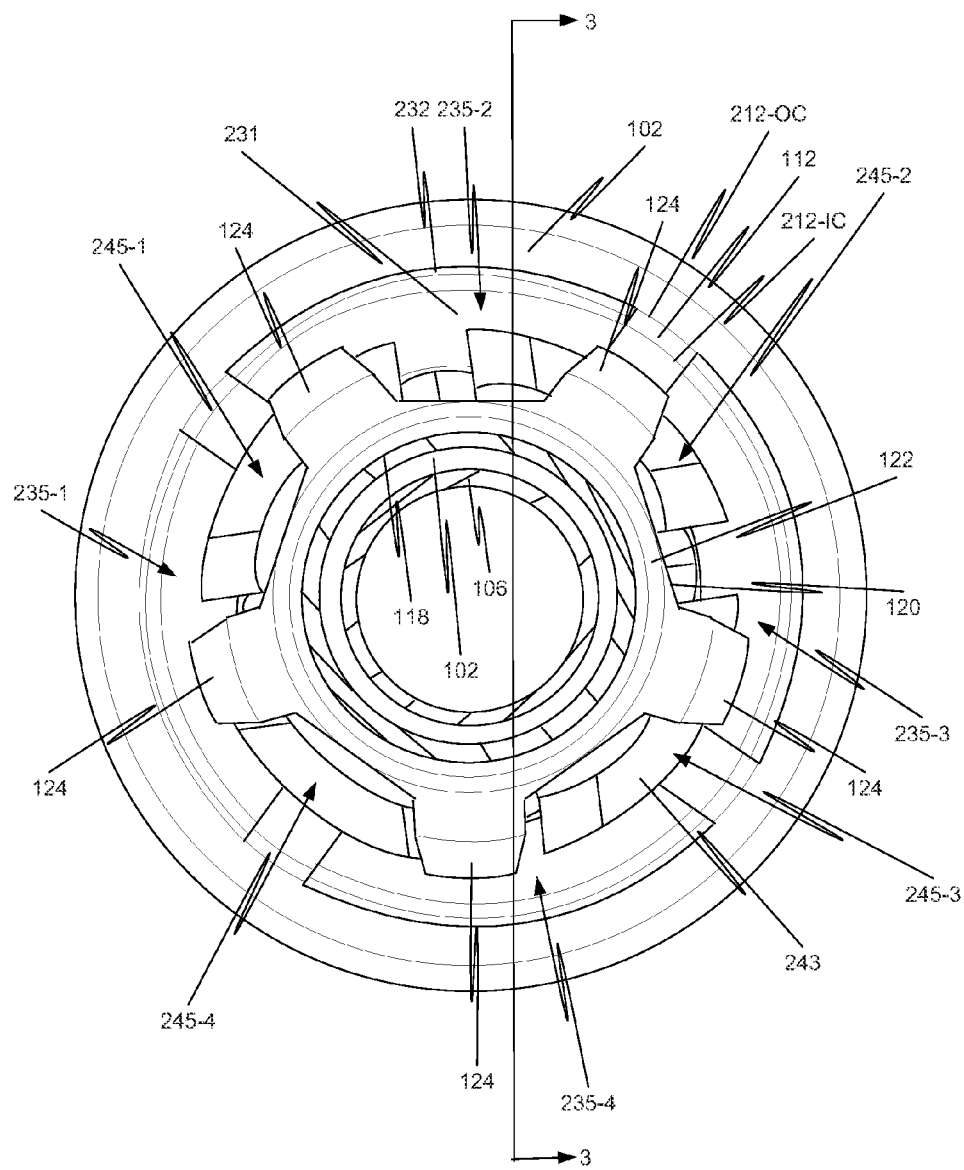
FIG. 2B is a sectional view of FIG. 2A taken at line 2B-2B looking in the distal direction (toward the tip).
Figure 3:
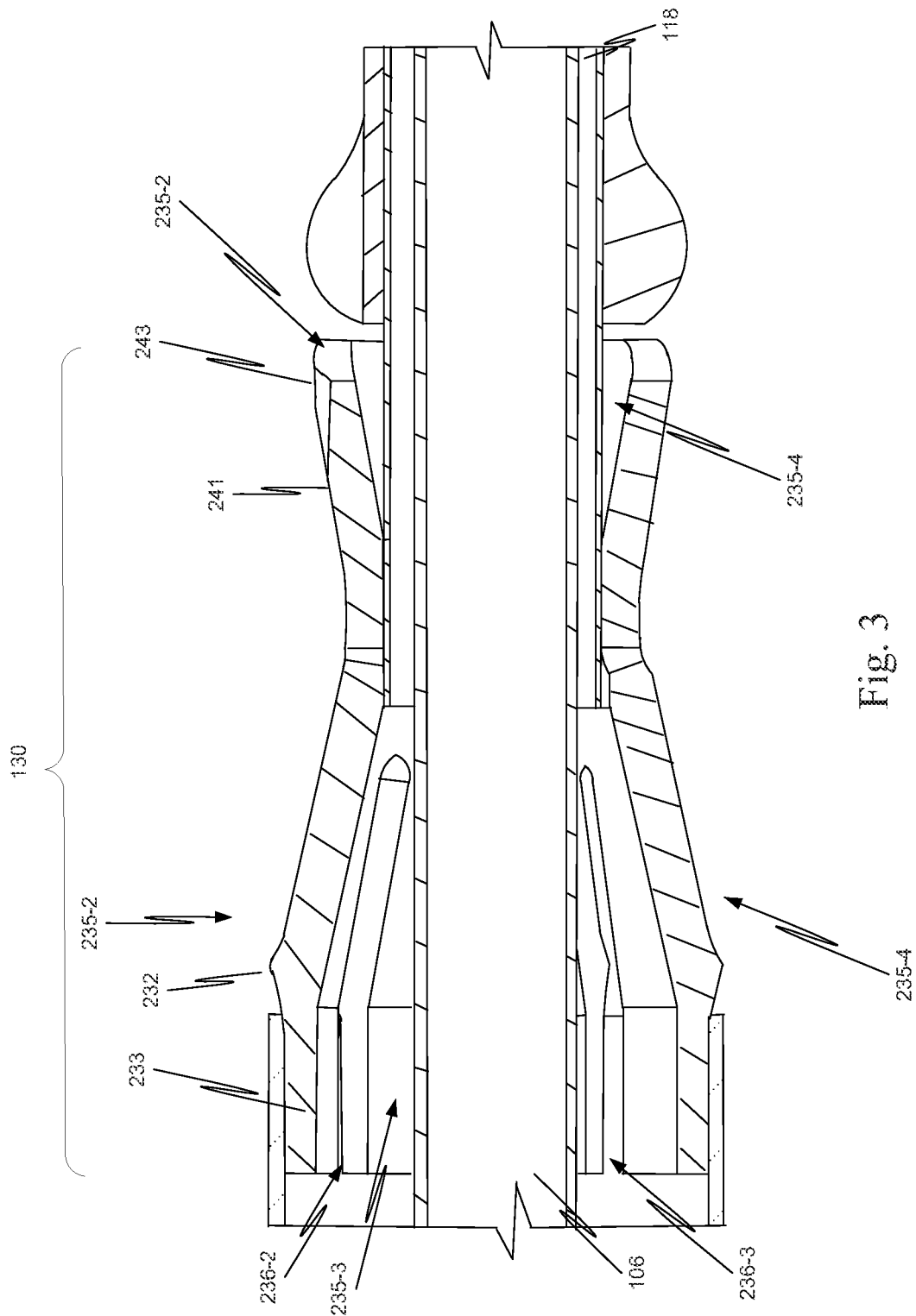
FIG. 3 is a side (non-centered) cross-sectional view of FIG. 2B taken at cut line 3-3.

In the drawings, the first digit of a reference number for an element indicates the figure in which the element with that reference number first appeared.

DETAILED DESCRIPTION

As illustrated in FIG. 1, in a first example, a component 130 is located on a distal portion of a stent delivery system 100. Component 130 includes both a retaining-sleeve landing component 132 and a stent ejection component 133. Retaining-sleeve landing component 132 includes a body 131 and a landing collar 136. Stent ejection component 133 includes body 131 and an ejection collar 135. Thus, in this example, retaining-sleeve landing component 132 and stent ejection component 133 share body 131.

While in the example of FIG. 1, component 130 includes both stent ejection component 133 and retaining-sleeve landing component 132, this is illustrative only and is not intended to be limiting. In view of this disclosure, a component can include only one of stent ejection component 133 and retaining-sleeve landing component 132. These alternatives follow directly from the example discussed more completely below with respect to FIGS. 1, 2A, 2B and 3. Thus, drawings of a delivery system with one of stent ejection component 133 and retaining-sleeve landing component 132 eliminated would be the same as these Figs. with the particular component eliminated. Thus, the alternative examples with one of the two components eliminated follow directly from and can be understood with reference to at least FIGS. 1, 2A, 2B, and 3.

As explained more completely below, landing collar 136 extends from body 131 in distal direction 191. Also, as explained more completely below, landing collar 136 automatically captures (engages, locks) the proximal end of tapered-tip retaining sleeve 112 when tapered tip 102 is moved in distal direction 191 to deploy a stent (or stent graft). Upon capture of the proximal end of tapered-tip retaining sleeve 112, landing collar 136 with tapered tip 102 attached has an atraumatic profile 134 when moving along the catheter in proximal direction 192.

The automatic capture of the proximal end of tapered-tip retaining sleeve 112 eliminates exposure to the square corner and potential sharp edge of the proximal end of tapered-tip retaining sleeve 112 and the need to re-capture a tip having sharp or catch promoting edges after deployment of the stent (or stent graft). Conventional stent delivery systems required recapture to reduce the risk of snagging the square corners and potentially sharp edges on the newly implanted device on high points in a tortuous anatomy when withdrawing the delivery system. The elimination of the tip capture sequence (procedure) decreases the total time required to use stent graft delivery system 100. A shorter procedure time has numerous benefits as is known to those knowledgeable in the field.

In addition, when retaining-sleeve landing component 132 with tapered tip 102 attached is withdrawn from the patient, atraumatic profile 134 inhibits tapered tip 102 from snagging on any part of the deployed stent graft. Thus, atraumatic profile 134 eliminates the problem of the delivery system snagging the stent, which was encountered when withdrawing a tapered tip in some conventional stent delivery systems.

As explained more completely below, ejection collar 135 extends from body 131 in proximal direction 192. Ejection collar 135 assists in automatically ejecting a proximal end of a stent (or stent graft) when, as explained more completely below, tapered tip 102 and the retaining sleeve 112 is moved in distal direction 191 to deploy the stent.

Specifically, ejection collar 135 assures that the crowns of the stent are released from spindle pins 124 of spindle 120. The individual elements of ejection collar 135 assist the natural self-expanding force of the stent to release the crowns from spindle pins 124. The additional force supplied by ejection collar 135 is sufficient to eject any crowns of the stent that may be stuck or binding on spindle pins 124 of spindle 120. Thus, ejection collar 135 helps in deploying the stent at the desired location with a particular orientation. Potential problems with the stent binding on the spindle pins are ameliorated with ejection collar 135.

FIG. 1 is an illustration of a distal end of a stent delivery system 100 without a stent and outer sheath in accordance with one example. Stent delivery system 100 includes a tapered tip 102 that is flexible and able to provide trackability in tight and tortuous vessels. Tapered tip 102 is illustrative only and is not intended to be limiting to this specific configuration. Other tip shapes such as bullet-shaped tips could also be used.

Tapered tip 102 includes a guide wire lumen therein, a primary sheath abutment 102a, and a stent retaining sleeve 112. The guide wire lumen allows passage of a guide wire through tapered tip 102.

A distal end of inner tube 106 is located within and secured to tapered tip 102, i.e., tapered tip 102 is mounted on inner tube 106. Inner tube 106 includes a guide wire lumen therein. The guide wire lumen of inner tube 106 is in fluid communication with the guide wire lumen of tapered tip 102 such that a guide wire can be passed through inner tube 106 and out distal end 102d of tapered tip 102.

Tapered tip 102 includes a tapered outer surface 108 that gradually increases in diameter in proximal direction 192. More particularly, tapered outer surface 108 has a minimum diameter at distal end 102d and gradually increases in diameter proximally, i.e., in the direction of the operator (or handle of stent-graft delivery system 100), from distal end 102d.

Tapered outer surface 108 extends proximally to a primary sheath abutment (shoulder) (surrounding shelf like surface) 102a of tapered tip 102. Primary sheath abutment 102a is an annular ring (shoulder) perpendicular to a longitudinal axis L of graft delivery system 100.

Stent retaining sleeve 112 is fixed to and may be integrally part of the proximal end of tapered tip 102, is mounted in primary sheath abutment 102a, and extends proximally from primary sheath abutment 102a. Generally, stent retaining sleeve 112, sometimes referred to as sleeve 112 or retaining sleeve 112, is at a proximal end of tapered tip 102. Stent retaining sleeve 112 extends proximally along longitudinal axis L of delivery system 100 from primary sheath abutment 102a.

In FIG. 1, stent retaining sleeve 112 is illustrated as a see through frame to illustrate features within sleeve 112. However, in other examples (FIGS. 4A-C), sleeve 112 is opaque. Sleeve 112 is made from, for example, stainless steel, nitinol, MP35N® alloy (a nonmagnetic, nickel-cobalt-chromium-molybdenum alloy), or a polymer. (MP35N® is a registered trademark of SPS Technologies, Inc.) The transparency of sleeve 112 is for ease of discussion only and is not limiting on the characteristics of stent retaining sleeve 112.

In this example, stent retaining sleeve 112 is a tube. However, the use of a tube is illustrative only and in not intended to limiting to this specific configuration. Other types of stent retaining sleeves can be used. For example, stent retaining sleeve 112, in another example, is a castellated sleeve such as that described in copending and commonly assigned U.S. patent application Ser. No. 12/426,020, entitled "CASTELLATED SLEEVE STENT-GRAFT DELIVERY SYSTEM AND METHOD," filed on Apr. 17, 2009, which is incorporated herein by reference in its entirety.

Stent delivery system 100 further includes a spindle tube 118, sometimes called an outer tube 118. Spindle 120 is affixed to a distal portion of outer tube 118. Spindle 120 includes a spindle body 122 having a cylindrical outer surface, and a plurality of spindle pins 124 protruding radially outward from spindle body 122. In this example, an outer edge surface of each spindle pin in plurality of spindle pins 124 has a rounded profile in a plane passing through both the longitudinal axis and the center of the spindle pin.

Spindle 120 is made from, for example, stainless steel, nitinol, MP35N® alloy, or a polymer. Also, inner tube 106 and outer tube 118 are made from, for example, stainless steel, nitinol, MP35N® alloy, or a braided polymer.

Spindle 120 is configured to slip inside of sleeve 112 such that spindle pins 124. The maximum radial height of spindle pins 124 is selected for a particular stent/stent graft. Thus, low profile spindle pins 124 are illustrative only and are not intended to be limiting. The maximum radial height for a spindle pin is directly adjacent to, or in contact with, an inner cylindrical surface 212-IC (FIG. 2B) of sleeve 112. Spindle pins 124 extend radially from spindle body 122 towards sleeve 112.

Generally, the maximum diameter to which spindle pins 124 extend from spindle body 122 is less than approximately equal to the diameter of the inner cylindrical surface 212-IC of sleeve 112 thereby allowing spindle pins 124 to fit inside of sleeve 112. An annular space exists between inner cylindrical surface 212-IC of sleeve 112 and spindle body 122. Another spindle and tapered tip suitable for use in delivery system 100 is described in commonly assigned, U.S. Patent Application Publication No. US 2008/0114442 A1, entitled "Delivery System for Stent-Graft with Anchoring Pins" having a filing date of Nov. 14, 2006, which is incorporated herein by reference in its entirety.

FIG. 2A is a close up view of component 130 and spindle 120 of FIG. 1. FIG. 2B is a sectional view looking in distal direction 191 from cut 2B-2B in FIG. 2A See FIG. 3 also, which is a cross-sectional view of FIG. 2B cut at 3-3.

Component 130 is fixedly attached to a distal end of spindle tube 118. In one example, both component 130 and spindle tube 118 are metal, e.g., stainless steel 304, and so component 130 is welded to the distal end of spindle tube 118. In another example, component 130 is formed from a polymer, and component 130 is bonded to the distal end of spindle tube 118. Component 130 is made from, for example, stainless steel, nitinol, MP35N® alloy, or a polymer.

The particular materials selected for spindle tube 118 and component 130 are not essential so long as spindle tube 118 functions in a manner equivalent to a spindle tube in a conventional delivery system, and component 130 has the features and functionality described herein. In addition, the particular method used to fixedly attach component 130 to the distal end of spindle tube 118 is not essential so long as component 130 remains attached to spindle tube 118 throughout the delivery of the stent and withdrawal of delivery system 100 from the patient.

As described above, component 130 includes two elements: (1) a retaining-sleeve landing component 132; and a stent ejection component 133. Both retaining-sleeve landing component 132 and stent ejection component 133 are described more completely below.

While in this example component 130 includes both of these elements, alternatively as explained above, a component can include only one of the two elements. Thus, the following description of component 130 is illustrative only and is not intended to be limiting to a component having both retaining-sleeve landing component 132 and stent ejection component 133.

Returning to retaining-sleeve landing component 132, landing collar 136 (FIGS. 1, 2A, 2B, 3) includes a plurality of cantilevered landing beams 235-1, 235-2, 235-3, 235-4 extending from body 131. Each cantilevered landing beam 235-i (where i ranges from 1 to N and N is the total number of cantilevered beans) in the plurality of cantilevered landing beams includes an inclined portion 231, a ridge 232, and a landing tab 233.

Each cantilevered landing beam 235-i has a length that extends in distal direction 191, along longitudinal axis L, from body 131, and has a width that is bounded by two slots extending from a proximal end to a distal end of cantilevered landing beam 235-i, e.g., cantilevered landing beam 235-1 is bounded by slots 236-4, 236-1. The distal end of each slot is open.

Thus, landing collar 136 includes a plurality of slots extending in distal direction 191 along longitudinal axis L. Also, each cantilevered landing beam 235-i includes an outer surface; and inner surface; two edge surfaces connecting the outer surface and the inner surface; and a distal end surface connecting the outer surface, inner surface and the two edge surface. The outer surface, inner surface and the two edge surface extend in the direction along longitudinal axis L. The two edge surfaces are separate and removed from each other.

Inclined portion 231 is the proximal part of landing collar 136 and transitions to ridge 232. Inclined portion 231 includes a tapered outer surface that gradually increases in radius from longitudinal axis L in distal direction 191. Inclined portion 231 is a portion of a frustum of a hollow cone with a centerline of the hollow cone coinciding with longitudinal axis L.

More particularly, the tapered outer surface has a minimum radius at a proximal end of inclined portion 231 and gradually increases in radius distally, i.e., in distal direction 191, from the proximal end of inclined portion 231. The slope and length of inclined portion 231 is selected to provide a desired atraumatic profile 134. Herein, an atraumatic profile is a profile that prevents injury to a patient and prevents snagging of a stent or stent-graft when component 130 and tapered tip 102 with sleeve 112 are withdrawn from the patient.

Each ridge 232 in the plurality of ridges has an outer radius that is greater than the radius of inner circumferential surface 212-IC of sleeve 112 when landing collar 136 is unconstrained or partially constrained. When component 130 is contained within sleeve 112, landing collar 136 is said to be totally constrained. Each of the plurality of cantilevered landing beams are elastically compressed radially inward (depressed) such that ridge 232 is within, contacts, and is held radially constrained by inner circumferential surface 212-IC of stent retaining sleeve 112.

In this initial position where component 130 is totally contained within sleeve 112, the outer radius of ridge 232 is approximately equal to the radius of inner circumferential surface 212-IC of stent retaining sleeve 112. Ridge 232 and the associated cantilevered landing beam are configured so that the frictional resistance force between ridge 232 and sleeve 112 is not so high that it prevents movement of sleeve 112 in distal direction 191 when deploying the stent.

When sleeve 112 is moved in distal direction 191 so that the proximal end of sleeve 112 is distal to ridge 232, the plurality of cantilevered landing beams are no longer totally constrained by sleeve 112. Thus, each cantilevered landing beam 235-i in the plurality of cantilevered landing beams springs radially outward from longitudinal axis L until landing tab 233 on cantilevered landing beam 235-i contacts inner circumferential surface 212-IC of sleeve 112. When the plurality of landing tabs is in contact with inner circumferential surface 212-IC of sleeve 112, component 130 is said to be partially constrained.

The radially outward force exerted by the plurality of cantilevered landing beams is sufficient that tapered tip 102 is securely held centered among the cantilevered beams by component 130 via the plurality of landing tabs. Thus, the radial expansion of the plurality of cantilevered landing beams causes the plurality of tabs to distally capture tapered tip 102.

In this partially constrained configuration, the plurality of cantilevered landing beams remain partially constrained by sleeve 112, i.e., an outer of radius of landing tab 233 is approximately equal to the radius of inner circumferential surface 212-IC of stent retaining sleeve 112.

In this partially constrained configuration, the outer radius of ridge 232 at least greater than the radius of inner circumferential surface 212-IC (FIG. 2B) of sleeve 112. Ideally, the outer radius of ridge 232 is equal to or greater than the radius of outer circumferential surface 212-OC (FIG. 2B) of sleeve 112. Also, the outer radius of ridge 232 is greater than the outer radius of the rest of body 131. Thus, atraumatic profile 134 is exposed when landing collar 136 is partially constrained by sleeve 112.

Factors considered in the design of the cantilevered landing beams include: (1) when the plurality of cantilevered landing beams are radially depressed and totally contained within sleeve 112, the radially outward force exerted by the plurality of ridges on inner circumferential surface 212-IC should not prevent distal movement of sleeve 112; and (2) when sleeve 112 is moved distal to the plurality of ridges, the radially outward force exerted by the plurality of landing tabs on the inner surface of sleeve 112 is sufficient to capture and retain tapered tip 102.

While in this example four cantilevered landing beams are used, in another example eight cantilevered landing beams were used. Thus, the number of cantilevered landing beams used herein in landing collar 136 is illustrative only and is not intended to be limiting to the number illustrated.

The ridge and slot elements of landing collar 136 allow landing collar 136 to have an element with a larger outer diameter than the inner diameter of sleeve 112 so that the plurality of landing tabs bend down toward longitudinal axis L when inserted in sleeve 112 and then recover when the proximal edge of sleeve 112 is moved distally past the plurality of ridges. Ridge 232 and inclined portion 231 form atraumatic profile 134, which provides a relatively smooth transition that does not snag on the deployed stent when delivery system 100 is withdrawn from the patient.

Returning to stent ejection component 133, ejection collar 135 (FIGS. 1, 2A, 2B, 3) includes a plurality of cantilevered ejection beams 245-1, 245-2, 245-3, 245-4 extending from body 131 in proximal direction 192. Each cantilevered ejection beam 245-$i$ (where i ranges from 1 to N and N is the total number of ejection cantilevered beans) in the plurality of cantilevered ejection beams includes an inclined portion 241 and a tab 243. Each cantilevered ejection beam 245-$i$ has a length that extends in proximal direction 192, along longitudinal axis L, from body 131, and has a width that is bounded by two slots extending from a proximal end of cantilevered ejection beam 245-$i$ into body 131, e.g., cantilevered ejection beam 245-1 is bounded by slots 246-4, 246-1. The proximal end of each slot is open.

Thus, ejection collar 135 includes a plurality of slots extending in proximal direction 192 along longitudinal axis L. Also, each cantilevered ejection beam 245-$i$ includes an outer surface; and inner surface; two edge surfaces connecting the outer surface and the inner surface; and a proximal end surface connecting the outer surface, inner surface and the two edge surface. The outer surface, inner surface and the two edge surface extend in proximal direction 192, along longitudinal axis L, from body 131. The two edge surfaces are separate and removed from each other.

Inclined portion 241 is a distal part of ejection collar 135 and transitions to ejection tab 243 that forms a proximal part of ejection collar 135. Inclined portion 241 includes a tapered outer surface that gradually increases in radius from longitudinal axis L in proximal direction 192. Inclined portion 241 is a portion of a frustum of a hollow cone with a centerline of the hollow cone coinciding with longitudinal axis L.

More particularly, the tapered outer surface has a minimum radius at a distal end of inclined portion 241, and gradually increases in radius proximally, i.e., in proximal direction 192, from the distal end of inclined portion 241. The slope and length of inclined portion 241 is selected to provide the desired radial motion of ejection tab 243.

Initially, the plurality of cantilevered ejection beams is held in a radially depressed (compressed) position by crowns of a stent which, in turn, are held radially compressed (restrained) by sleeve 112. In this initial position when component 130 is totally contained within sleeve 112, the plurality of ejection tabs is constrained under the crowns of the stent, so that each ejection cantilevered ejection beam 245-$i$ is radially elastically compressed (depressed) towards longitudinal axis L.

When sleeve 112 is moved in distal direction 191 so that the proximal end of sleeve 112 is distal to the plurality of cantilevered ejection beams, the plurality of cantilevered ejection beams is no longer radially constrained by sleeve 112. Thus, each cantilevered ejection beam 245-$i$ in the plurality of cantilevered ejection beams springs radially outward from longitudinal axis L. The outward radial motion, i.e., motion away from longitudinal axis L, causes tab 243 on cantilevered ejection beam 245-$i$ to assure that the stent crown moves radially outward. The radially outward force exerted by the plurality of ejection tabs on the stent is sufficient to assure that the stent is deployed from spindle pins 124 of spindle 120.

While in this example four cantilevered ejection beams are used, in another example eight cantilevered ejection beams were used. Thus, the number of cantilevered ejection beams used herein in ejection collar 135 is illustrative only and is not intended to be limiting.

Figure 4A:
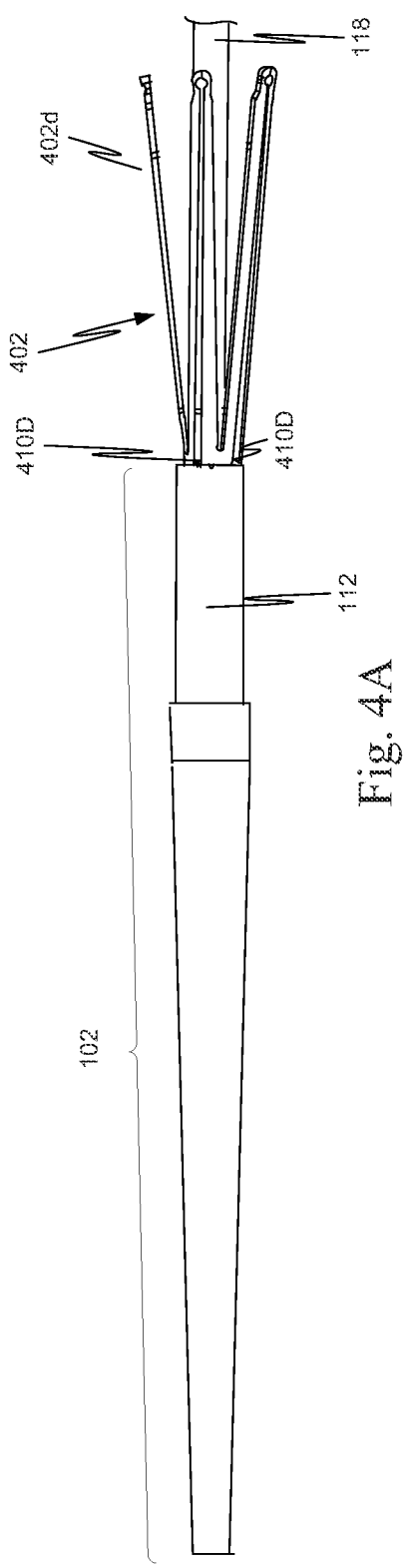
FIGS. 4A to 4C schematically illustrate progressive steps in the deployment of a stent by the delivery system of FIG. 1.

FIG. 4A is a view of stent delivery system 100 of FIG. 1 including a stent 402 located within a retractable primary sheath (not shown) in a pre-deployment un-retracted position. In one example, stent 402 is a supra renal stent. However, in view of this disclosure, component 130 can be used with a stent or stent-graft of interest and the corresponding delivery system.

The primary sheath is a hollow tube and defines a lumen therein through which tapered tip 102 with stent retaining sleeve 112, spindle tube 118 and inner tube 106 extend. To initiate the deployment of stent 402, the primary sheath is moved proximally along longitudinal axis L, sometimes called refracted, relative to spindle tube 118/spindle 120 and thus deploys a portion of stent 402 as discussed further below.

In FIG. 4A, the primary sheath has already been withdrawn and so is not shown. In another example, the primary sheath is withdrawn far enough to expose sleeve 112, but not far enough to expose a distal end 402$d$ of stent 402. In this alternative example, distal end 402$d$ of stent 402 remains constrained until after the proximal end of stent 402 is deployed.

In one example, stent 402 is a self-expanding stent such that stent 402 self-expands upon being released from its radially constrained position. In accordance with this example, stent 402 is a resilient self-expanding structure, e.g., formed of super elastic self-expanding memory material such as nitinol.

Figure 4B:
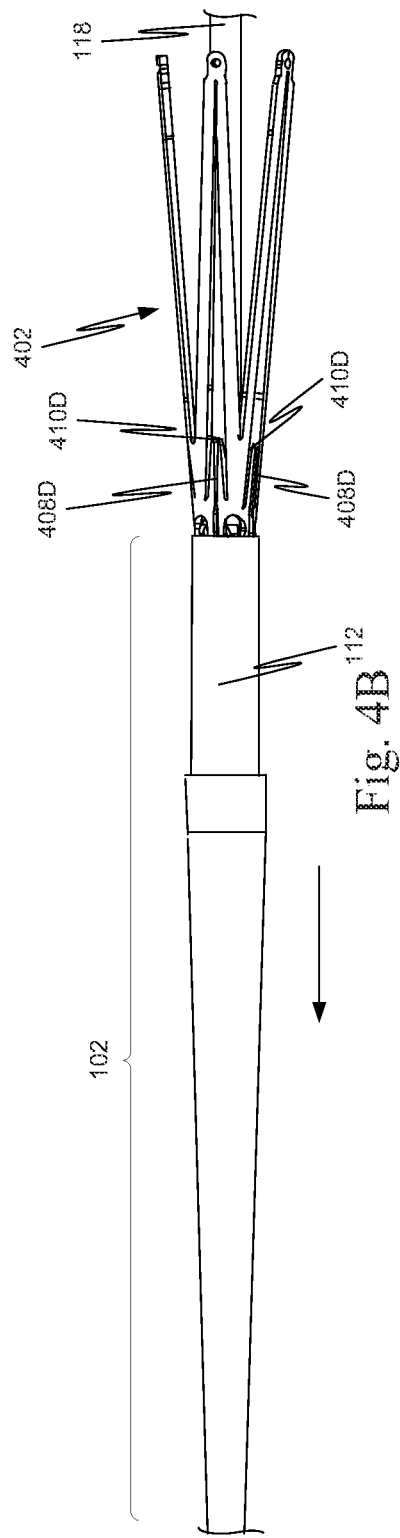

While it is obscured by opaque sleeve 112, in FIGS. 4A and 4B, a proximal part of stent 402 is in a radially constrained configuration over spindle tube 118 and spindle 120. The proximal apexes of stent 402 are locked around spindle pins 124 and between inner circumferential surface 212-IC of sleeve 112 and spindle body 122.

Thus, after the primary sheath is withdrawn, the proximal apexes, sometimes called crowns, of stent 402 are radially constrained and held in position (captured) on spindle pins 124 by sleeve 112. Due to the retraction of the primary sheath, a distal portion of stent 402, which is proximal to the proximal end of sleeve 112, is exposed and partially deployed (expanded).

Sleeve 112 does not cover (exposes) distal tips 410D of anchor pins 408D. Sleeve 112 extends distally only partially over anchor pins 408D. This prevents distal tips 410D, e.g., sharp tips, from engaging (digging into, scratching, gouging) sleeve 112. Refer to U.S. Patent Application Publication No. 2008/0114442 dated May 15, 2008, hereby incorporated by reference in its entirety herein.

Figure 4C:
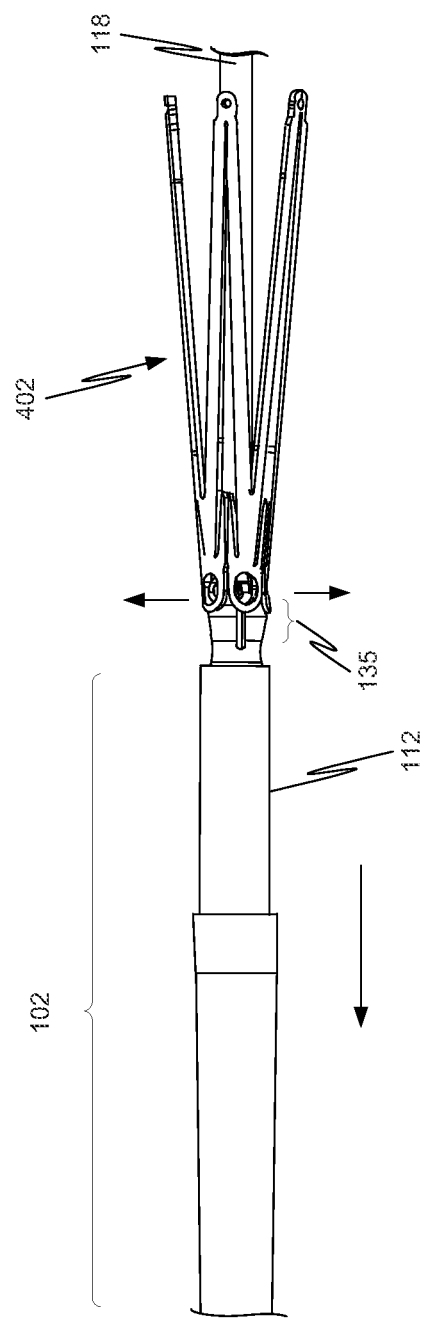

In FIG. 4B, inner tube 106 has been advanced relative to spindle 120, which has simultaneously moved tapered tip 102 with sleeve 112 in distal direction 191 to expose more of the proximal end of stent 402. In FIG. 4C, inner tube 106 is shown having been advanced further relative to spindle 120, which moves tapered tip 102 with sleeve 112 further in distal direction 191 to expose the proximal end of stent 402 and to eject the crowns from spindle pins 124 of spindle 120.

FIG. 4C illustrates the instant just after the proximal edge of sleeve 112 was moved to expose the proximal end of stent 420, but before the proximal end of stent 420 starts to expand. Upon being released from the constraint of sleeve 112, the proximal end of stent 402 self expands (not shown). Also, ejection collar 135 assists in forcing the crowns of stent 402 off pins 124 of spindle 120 so that the proximal end of stent 402 is successfully deployed.

When inner tube 106 is advanced even further in distal direction 191 relative to spindle 120, tapered tip 102 with sleeve 112 is moved in the distal direction so that the proximal end edge of sleeve 112 moves beyond the plurality of ridges and is distally and centeringly captured by the plurality of landing tabs of landing collar 136. This configuration is illustrated in FIG. 1.

After tapered tip 102 with sleeve 112 is captured, delivery system 100 is withdrawn from the patient. As described above, atraumatic profile 134 prevents snagging the stent and anatomical structures as tapered tip 102 with sleeve 112 is withdrawn.

As illustrated in FIGS. 5A, 5B, another example of a retaining-sleeve landing component 532 includes a body 531 and a landing collar 536. Landing collar 536 extends from body 531 in distal direction 591. Also, as explained more completely below, a portion 538B (FIG. 5B) of landing collar 536 remains in a proximal end of tapered-tip retaining sleeve 512 when tapered tip 502 is moved in distal direction 591 to deploy a stent (or stent graft).

Thus, in the deployment of the stent, tapered tip 502 is automatically maintained centered about longitudinal axis 590, which is sometimes referred to as being automatically captured. Following deployment of the stent, landing collar 536 with tapered tip 502 attached has an atraumatic profile 534 in proximal direction 592.

Also, in this example, the automatic capture of the proximal end of tapered-tip retaining sleeve 512 eliminates exposure to the square corner and potential sharp edge of the proximal edge of tapered-tip retaining sleeve 512 and the need to capture a tip having such sharp or catch promoting edges after deployment of the stent (or stent graft). The elimination of the tip capture sequence decreases the time required for the procedure being performed using stent delivery system 500.

In addition, when retaining-sleeve landing component 532 with tapered tip 502 attached is withdrawn from the patient, atraumatic profile 534 inhibits tapered tip 502 from snagging on the deployed stent. Thus, atraumatic profile 534 eliminates the problem of the delivery system snagging the stent, which was encountered when withdrawing a tapered tip in some conventional stent delivery systems.

FIGS. 5A, 5B are illustrations of a distal end of a stent delivery system 500 without a stent and outer sheath in accordance with one example. The distal end of stent delivery system 500 includes a tapered tip 502 that is flexible and able to provide trackability in tight and tortuous vessels. Tapered tip 502 is illustrative only and is not intended to be limiting to this specific configuration. Other tip shapes such as bullet-shaped tips could also be used.

Tapered tip 502 includes a guide wire lumen therein, a primary sheath abutment 502a, and a stent retaining sleeve 512. The guide wire lumen allows passage of a guide wire through tapered tip 502.

A distal end of inner tube 506 (FIG. 5B) is located within and secured to tapered tip 502, i.e., tapered tip 502 is mounted on inner tube 506. Inner tube 506 includes a guide wire lumen therein. The guide wire lumen of inner tube 506 is in fluid communication with the guide wire lumen of tapered tip 502 such that a guide wire can be passed through inner tube 506 and out the distal end of tapered tip 502.

Tapered tip 502 includes a tapered outer surface 508 that gradually increases in diameter in proximal direction 592. More particularly, tapered outer surface 508 has a minimum diameter at the distal end and gradually increases in diameter proximally, i.e., in the direction of the operator (or handle of stent-graft delivery system 500), from the distal end.

Tapered outer surface 508 extends proximally to a primary sheath abutment 502a (shoulder) (surrounding shelf like surface) of tapered tip 502. Primary sheath abutment 502a is an annular ring (shoulder) perpendicular to a longitudinal axis 590 of graft delivery system 500.

Stent retaining sleeve 512 is fixed to and may be integrally part of the proximal end of tapered tip 502 and mounted in primary sheath abutment 502a, and extends proximally from primary sheath abutment 502a. Generally, stent retaining sleeve 512, sometimes referred to as sleeve 512 or retaining sleeve 512, is at a proximal end of tapered tip 502. Stent retaining sleeve 512 extends proximally along longitudinal axis 590 of delivery system 500 from primary sheath abutment 502a.

In FIGS. 5A, 5B, stent retaining sleeve 512 is illustrated as a see through frame to illustrate features within sleeve 512. However, in other examples, sleeve 512 is opaque. Sleeve 512 is made from, for example, stainless steel, nitinol, MP35N® alloy (a nonmagnetic, nickel-cobalt-chromium-molybdenum alloy), or a polymer. (MP35N® is a registered trademark of SPS Technologies, Inc.) The transparency of sleeve 512 is for ease of discussion only and is not limiting on the characteristics of stent retaining sleeve 512.

In this example, stent retaining sleeve 512 is a tube. However, the use of a tube is illustrative only and in not intended to limiting to this specific configuration. Other types of stent retaining sleeves can be used. For example, stent retaining sleeve 512, in another example, is a castellated sleeve such as that described in copending and commonly assigned U.S. patent application Ser. No. 12/426,020, entitled "CASTELLATED SLEEVE STENT-GRAFT DELIVERY SYSTEM AND METHOD," filed on Apr. 17, 2009, which is incorporated herein by reference in its entirety.

Stent delivery system 500 further includes a spindle tube 518, sometimes called an outer tube 518. Spindle 520 is affixed to a distal portion of outer tube 518. Spindle 520 includes a spindle body 522 having a cylindrical outer surface, and a plurality of spindle pins 524 protruding radially outward from spindle body 522. In this example, an outer edge surface of each spindle pin in plurality of spindle pins 524 has a rounded profile in a plane passing through both longitudinal axis 590 and the center of the spindle pin.

Spindle 520 is made from, for example, stainless steel, nitinol, MP35N® alloy, or a polymer. Also, inner tube 506 and outer tube 518 are made from, for example, stainless steel, nitinol, MP35N® alloy, or a braided polymer.

Spindle 520 is configured to slip inside of sleeve 512 such that spindle pins 524 are within sleeve 512 (FIG. 5A) prior to deployment of the stent. The maximum radial height of spindle pins 524 is selected for a particular stent/stent graft. Thus, low profile spindle pins 524 are illustrative only and are not intended to be limiting.

The maximum radial height for a spindle pin is directly adjacent to, or in contact with, an inner cylindrical surface of sleeve 512. Spindle pins 524 extend radially from spindle body 522 towards sleeve 512. Generally, the maximum diameter to which spindle pins 524 extend from spindle body 522 is less than approximately equal to the diameter of the inner cylindrical surface of sleeve 512 allowing spindle pins 524 to fit inside of sleeve 512. An annular space exists between the inner cylindrical surface of sleeve 512 and spindle body 522. Another spindle and tapered tip suitable for use in delivery system 500 is described in commonly assigned, U.S. Patent Application Publication No. US 2008/0114442 A1, entitled "Delivery System for Stent-Graft with Anchoring Pins" of Mitchell et al. having a filing date of Nov. 14, 2006, which was previously incorporated herein by reference in its entirety.

Retaining-sleeve landing component 532 is fixedly attached to a distal end of spindle tube 518. In one example, retaining-sleeve landing component 532 is integral with spindle 520, i.e., spindle 520 and retaining-sleeve landing component 532 are a single part. Retaining-sleeve landing component 532 is made from, for example, stainless steel, nitinol, MP35N® alloy, or a polymer.

The particular materials selected for spindle tube 518 and retaining-sleeve landing component 532 are not essential so long as spindle tube 518 functions in a manner equivalent to a spindle tube in a conventional delivery system, and retaining-sleeve landing component 532 the features and functionality described herein. In addition, the particular method used to fixedly attach retaining-sleeve landing component 532 to the distal end of spindle tube 518 is not essential so long as ejection retaining-sleeve landing component 532 remains attached to spindle tube 518 throughout the delivery of the stent and withdrawal of delivery system 500 from the patient.

A distal portion 538 of landing collar 536 (FIGS. 5B) is a hollow cylinder with an axis coincident with longitudinal axis 590. Thus, the outer circumferential surface of distal landing collar portion 538 has a substantially uniform radius. Here, substantially uniform means uniform to within manufacturing tolerances. Distal landing collar portion 538 has a length x1 extending proximally along longitudinal axis 590 from the distal end surface of landing collar 536.

An inclined portion 536_I is a proximal part of landing collar 536 and transitions from body 531 to distal landing collar portion 538. Inclined portion 536_I includes a tapered outer surface that gradually increases in radius from longitudinal axis 590 in distal direction 591. Inclined portion 536_I is a portion of a frustum of a hollow cone with a centerline of the hollow cone coinciding with longitudinal axis 590.

More particularly, the tapered outer surface of inclined portion 536_I has a minimum radius at a proximal end of portion 536_I and gradually increases in radius distally, i.e., in distal direction 591, from the proximal end of portion 536_I. The slope and length of inclined portion 536_I is selected to provide a desired atraumatic profile 534. Again, an atraumatic profile is a profile that prevents injury to a patient and prevents snagging of a stent or stent-graft when retaining-sleeve landing component 532 and tapered tip 502 with sleeve 512 are withdrawn from the patient.

In an initial position (FIG. 5A), retaining-sleeve landing component 532 is totally contained within sleeve 512. An outer radius of landing collar 536 is approximately equal to a radius of the inner circumferential surface of stent retaining sleeve 512. The outer radius of landing collar 536 is selected so that the frictional resistance force between the outer circumferential surface of landing collar distal portion 538 and sleeve 512 is not so high that it prevents movement of sleeve 512 in distal direction 591 when deploying the stent.

When sleeve 512 is moved in distal direction 591a distance x to deploy the stent (stent graft), a part 538B of landing collar distal portion 538 remains within the proximal end of retaining sleeve 512. In one example, the length of retaining sleeve and length x1 of landing collar distal portion 538 are selected in combination. The length of retaining sleeve 512 is selected so that when shoulder 502a contacts the distal edge surface of landing collar distal portion 538, the proximal edge of retaining sleeve 512 is only partially over any anchor pins of the stent constrained by retaining sleeve 512. This prevents the distal tips of the anchor pins, e.g., sharp tips, from engaging (digging into, scratching, gouging) sleeve 512. Refer to U.S. Patent Application Publication No. 2008/0114442 dated May 15, 2008, which was previously incorporated by reference in its entirety herein.

Length x1 of landing collar distal portion 538 is selected to that when tapered tip 502 and consequently retaining sleeve 512 are moved distance x to deploy a stent, a sufficient part 538B of landing collar distal portion 538 remains within retaining sleeve 512 so that retaining sleeve 512 remains centered about longitudinal axis 590. With sleeve 512 centered on landing collar 536, the combination has atraumatic profile 534 when delivery system 500 is retracted. Atraumatic profile 534 provides a relatively smooth transition that does not snag on the deployed stent when delivery system 500 is withdrawn from the patient.

Figure 6A:
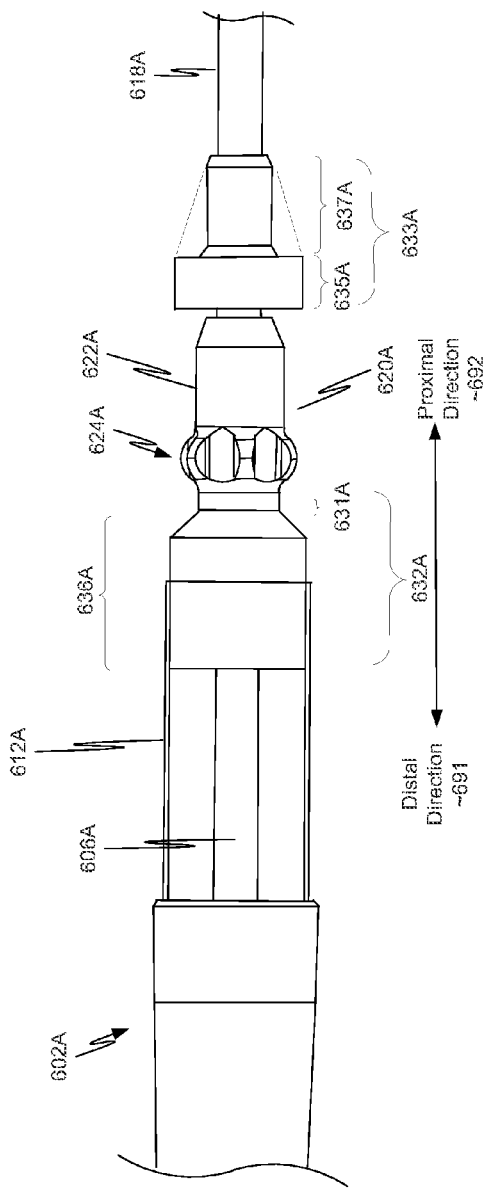
FIG. 6A illustrates another stent graft delivery system that includes both a retaining-sleeve landing component and a stent ejection component, but the retaining-sleeve landing component is separate and removed from stent ejection component.

Yet another example is illustrated in FIG. 6A. In this example, stent graft delivery system 600A includes both a retaining-sleeve landing component 632A and a stent ejection component 633A. Retaining-sleeve landing component 632A includes a body 631A and a landing collar 636A. Stent ejection component 633 includes a body 637A and an ejection collar 635A. Thus, in this example, retaining-sleeve landing component 632A is separate and removed from stent ejection component 633A in contrast to the example in FIG. 1.

As explained more completely below, ejection collar 635A extends from body 637A in distal direction 691. Ejection collar 635A assists in automatically ejecting a proximal end of a stent (or stent graft) when, as explained more completely below, tapered tip 602A and retaining sleeve 612A are moved in distal direction 691 to deploy the stent.

Specifically, ejection collar 635A assures that the crowns of the stent are released from spindle pins 624A of spindle 620A when the proximal end of the stent is released. Ejection collar 635A assists the natural self-expanding force of the stent to release the crowns from spindle pins 624A. The additional force supplied by ejection collar 635A is sufficient to eject any crowns of the stent that may be stuck or binding on spindle pins 624A of spindle 620A. Thus, ejection collar 635A helps in deploying the stent at the desired location with a particular orientation. Previous problems with the stent binding on the spindle pins are ameliorated with ejection collar 635A.

FIG. 6A is an illustration of a distal end of a stent delivery system 600 without a stent and outer sheath in accordance with one example. Tapered tip 602A, retaining sleeve 612A, retaining-sleeve landing component 632, spindle 620A, spindle tube 618A, and inner tube 606A are equivalent to tapered tip 502, retaining sleeve 512, retaining-sleeve landing component 532, spindle 520A, spindle tube 518A, and inner tube 506, respectively. Thus, the above description of tapered tip 502, retaining sleeve 512, retaining-sleeve landing component 532, spindle 520A, spindle tube 518A, and inner tube 506 is incorporated herein by reference for tapered tip 602A, retaining sleeve 612A, retaining-sleeve landing component 632, spindle 620A, spindle tube 618A, and inner tube 606A, respectively, and is not repeated.

Stent ejection component 633A is fixedly mounted on spindle shaft 618A proximal to spindle 620A. A distal end surface of ejection collar 635A is adjacent a proximal end of body 622A of spindle 620A. Body 637A extends from ejection collar 635A in proximal direction 692.

The dotted lines from the proximal end of body 637A to the proximal edge of ejection collar 635A are not a part of this example. The dotted lines represent an alternative implementation of body 637A, which has an atraumatic profile when spindle tube 618A is retracted in the proximal direction after stent deployment.

In this example, ejection collar 635A, in an uncompressed state, is a hollow cylinder with an axis coincident with the longitudinal axis of spindle tube 618A. The outer circumferential surface of ejection collar 635A has a substantially uniform radius. Here, substantially uniform means uniform to within manufacturing tolerances. The outer radius of ejection collar 635A is not less than the outer radius of spindle pins 624A, in one example. Ejection collar 635A is made from an elastically deformable material. In one example, both body 637A and ejection collar 635A are made from the same elastically deformable material as an integral part. One suitable elastically deformable material is silicone. Stent ejection component 633A is bonded to spindle shaft 618A.

Figure 6B:
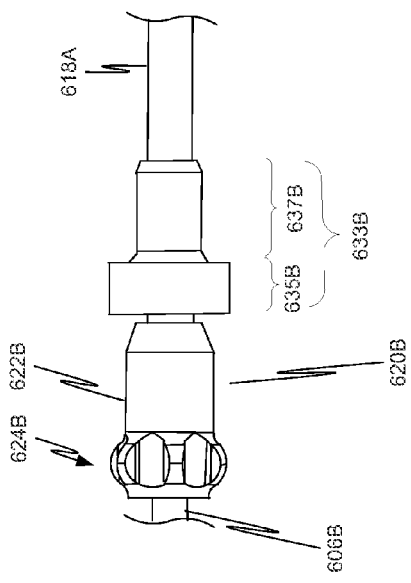
FIG. 6B illustrates an example of a stent graft delivery system that includes only a stent ejection component.

The distal end of stent graft delivery system 600B in FIG. 6B is the same as the distal end of stent graft delivery system 600A in FIG. 6B except retaining-sleeve landing component 632A has been eliminated. Thus, elements 606B, 624B, 622B, 620B, 633B, 635B, 637B, 618B are the same as elements 606A, 624A, 622A, 620A, 633A, 635A, 637A, 618A, respectively. The example of FIG. 6B includes a stent ejection component, but no retaining-sleeve landing component.

In FIG. 7A, stent ejection component 733 on spindle shaft 718 is the same as stent ejection components 633A (FIG. 6A), 633B (FIG. 6B). Initially, stent 702 is located within a retractable primary sheath (not shown) in a pre-deployment unretracted position. In one example, stent 702 is a supra renal stent. However, in view of this disclosure, stent ejection component 733 can be used with a stent or stent-graph of interest and the corresponding delivery system.

The primary sheath is a hollow tube and defines a lumen therein through which the tapered tip with the stent retaining sleeve, spindle tube and inner tube extend. Stent 702 is compressed on spindle pins 724 of spindle 720; stent ejection component 733 is elastically deformed by the compressed struts of the stent; and stent 702 is initially held in place in part by the primary sheath.

To initiate the deployment of stent 702, the primary sheath is moved proximally along the longitudinal axis, sometimes called retracted, relative to the spindle tube/spindle/stent ejection component and thus deploys a distal portion of stent 702.

In FIG. 7A, the primary sheath has already been withdrawn and so is not shown. In this example, stent 702 is a self-expanding stent such that stent 702 self-expands upon being released from its radially constrained position. In accordance with this example, stent 702 is a resilient self-expanding structure, e.g., formed of super elastic self-expanding memory material such as nitinol.

While it is partially obscured by opaque sleeve 712, in FIG. 7A, a proximal part of stent 702 is in a radially constrained configuration over spindle tube 718, spindle 720, and elastically deformed ejection collar 735. The proximal apexes of stent 702 are locked around spindle pins 722 and locked between an inner circumferential surface of sleeve 712 and spindle body 722.

Thus, after the primary sheath is withdrawn, the proximal apexes, sometimes called crowns, of stent 702 are radially constrained and held in position (captured) on spindle pins 724 by sleeve 712. Due to the retraction of the primary sheath, a distal portion of stent 702, which is proximal to the proximal end of sleeve 712, is exposed and partially deployed (expanded).

When retaining sleeve 712 is moved in the distal direction so that the proximal end of sleeve 712 is distal to spindle 720 (FIG. 7B), the proximal end of stent 702 is no longer held compressed by sleeve 712. Similarly, ejection collar 733 is no longer held compressed and energy stored in the elastically deformed ejection collar 733 is applied to cause it to spring radially outward from the longitudinal axis. The outward radial motion, i.e., motion away from the longitudinal axis, causes the outer circumferential surface of ejection collar 735 to assure that the stent crowns moves radially outward. The radially outward force exerted by expanding ejection collar 735 on stent 702 is sufficient to assure that stent 702 is deployed from spindle pins 724 of spindle 720.

FIG. 7B is an illustration of the configuration of the after ejection collar 735 which has radially expanded to its uncompressed relaxed state. Ejection collar 735 lifts stent strut 702B so that the crown is removed from the corresponding spindle pin of spindle 720.

We claim:

1. A graft delivery system comprising:
   a spindle tube;
   a spindle mounted on the spindle tube;
   a retaining-sleeve landing component fixed to the spindle tube distal of the spindle, the retaining-sleeve landing component having a body and a landing collar extending distally from the body;
   a tube slidably extending through the spindle tube, the spindle and the retaining-sleeve landing component, the tube having a distal end; and
   a tip mounted on the distal end of the tube, the tip having a proximal portion that defines a retaining sleeve, wherein the retaining sleeve is slidably movable over the landing collar of the retaining-sleeve landing component; wherein the retaining-sleeve landing component and the spindle are a single integral element with the spindle having a plurality of spindle pins disposed proximal of the body; and wherein the distal portion of the landing collar has a length so that at least part of the distal portion remains within the retaining sleeve following a stent deployment.

2. The graft delivery system of claim 1, wherein the landing collar further comprises:
   a plurality of cantilevered landing beams extending distally from the body.

3. The graft delivery system of claim 2, wherein adjacent cantilevered landing beams are separated by a slot.

4. The graft delivery system of claim 2, wherein each cantilevered landing beam, in the plurality of cantilevered landing beams, includes an atraumatic profile along a proximal portion thereof.

5. The graft delivery system of claim 2, wherein at least one cantilevered landing beam in the plurality of cantilevered landing beams includes a ridge and an inclined proximal portion extending from the body to the ridge.

6. The graft delivery system of claim 5, wherein the at least one cantilevered beam includes a landing tab extending distally from the ridge.

7. The graft delivery system of claim 6, wherein an outer radius of the ridge is greater than an outer radius of the landing tab.

8. The graft delivery system of claim 1, wherein
the landing collar includes an element with an outer radius greater than an inner radius of the retaining sleeve.

9. The graft delivery system of claim 8, wherein the element of the landing collar is a ridge.

10. The graft delivery system of claim 9 wherein the outer radius of the ridge is greater than an outer radius of the body such that a proximal portion of the landing collar extending distally from the body to the ridge has a tapered outer surface that gradually increases in radius from the body to the ridge and thereby defines an atraumatic profile between the body and the ridge.

11. The graft delivery system of claim 1, wherein each spindle pin in the plurality of spindle pins has a rounded profile.

12. The graft delivery system of claim 1, wherein a proximal portion of the landing collar has an atraumatic profile.

13. The graft delivery system of claim 12, wherein the proximal portion comprises an inclined portion.

14. The graft delivery system of claim 1, wherein the landing collar comprises a cylinder having an outer circumferential surface of substantially uniform radius.

15. The graft delivery system of claim 1, wherein the spindle includes a plurality of spindle pins disposed proximal of the body and wherein the landing collar includes a proximal portion having an atraumatic profile and a distal portion comprising a hollow cylinder having an outer circumferential surface of substantially uniform radius.

16. The graft delivery system of claim 1, wherein
the landing collar includes a distal portion with an outer radius approximately equal to an inner radius of the retaining sleeve.

17. The graft delivery system of claim 16, wherein the landing collar includes a proximal portion extending distally from the body to the distal portion that has a tapered outer surface that gradually increases in radius from the body to the distal portion such that the proximal portion has an atraumatic profile.

* * * * *